(12) United States Patent
Dennett, Jr. et al.

(10) Patent No.: US 9,919,007 B2
(45) Date of Patent: Mar. 20, 2018

(54) DUAL USE ORAL PHARMACEUTICAL COMPOSITION TABLETS OF SULFATE SALTS AND METHODS OF USE THEREOF

(71) Applicant: Braintree Laboratories, Inc., Braintree, MA (US)

(72) Inventors: Edmund V. Dennett, Jr., Walpole, MA (US); David S. Wells, Shrewsbury, MA (US)

(73) Assignee: Braintree Laboratories, Inc., Braintree, MA (US)

( * ) Notice: Subject to any disclaimer, the term of this patent is extended or adjusted under 35 U.S.C. 154(b) by 0 days.

(21) Appl. No.: 14/774,018

(22) PCT Filed: Mar. 14, 2014

(86) PCT No.: PCT/US2014/028805
§ 371 (c)(1),
(2) Date: Sep. 9, 2015

(87) PCT Pub. No.: WO2014/144407
PCT Pub. Date: Sep. 18, 2014

(65) Prior Publication Data
US 2016/0030473 A1    Feb. 4, 2016

Related U.S. Application Data

(60) Provisional application No. 61/798,759, filed on Mar. 15, 2013.

(51) Int. Cl.
| | | |
|---|---|---|
| *C01D 5/00* | (2006.01) | |
| *A61K 9/28* | (2006.01) | |
| *A61K 9/20* | (2006.01) | |
| *A61K 33/04* | (2006.01) | |
| *A61K 9/00* | (2006.01) | |
| *A61K 33/06* | (2006.01) | |

(52) U.S. Cl.
CPC ............ *A61K 33/04* (2013.01); *A61K 9/0053* (2013.01); *A61K 9/0095* (2013.01); *A61K 9/2018* (2013.01); *A61K 9/2027* (2013.01); *A61K 9/2031* (2013.01); *A61K 9/2095* (2013.01); *A61K 9/2853* (2013.01); *A61K 9/2893* (2013.01); *C01D 5/00* (2013.01); *A61K 33/06* (2013.01)

(58) Field of Classification Search
None
See application file for complete search history.

(56) References Cited

U.S. PATENT DOCUMENTS

| | | |
|---|---|---|
| 3,873,694 A | 3/1975 | Kanig |
| 4,292,299 A | 9/1981 | Suzuki et al. |
| 4,454,108 A | 6/1984 | Lida et al. |
| 4,665,081 A | 5/1987 | Doi et al. |
| 4,753,801 A | 6/1988 | Oren et al. |
| 4,837,030 A | 6/1989 | Valorose, Jr. et al. |
| 4,950,484 A * | 8/1990 | Olthoff ............... A61K 9/2054 424/464 |
| 4,959,222 A | 9/1990 | Nadland et al. |
| 4,975,286 A | 12/1990 | Hechter |
| 5,077,048 A | 12/1991 | Kimura et al. |
| 5,124,144 A | 6/1992 | Giorgetti et al. |
| 5,211,958 A | 5/1993 | Akkerboom et al. |
| 5,274,001 A | 12/1993 | Borody |
| 5,498,425 A | 3/1996 | Wood et al. |
| 5,710,183 A | 1/1998 | Halow |
| 5,858,403 A | 1/1999 | Borody et al. |
| 5,958,458 A | 9/1999 | Norling et al. |
| 6,133,237 A | 10/2000 | Noll et al. |
| 6,162,464 A | 12/2000 | Jacob et al. |
| 6,200,604 B1 | 3/2001 | Pather et al. |
| 6,235,745 B1 | 5/2001 | Megens |
| 6,391,335 B1 | 5/2002 | Pather et al. |
| 6,509,036 B2 | 1/2003 | Pather et al. |
| 6,645,481 B1 | 11/2003 | Cleveland et al. |
| 6,887,492 B2 | 5/2005 | Kay et al. |
| 6,946,149 B2 | 9/2005 | Cleveland |
| 7,169,381 B2 | 1/2007 | Barras et al. |
| 7,291,324 B2 | 11/2007 | Dennett, Jr. et al. |
| 7,687,075 B2 | 3/2010 | Skiendzielewski et al. |
| 7,993,682 B2 | 8/2011 | Borody et al. |

(Continued)

FOREIGN PATENT DOCUMENTS

| | | |
|---|---|---|
| CN | 101087593 A | 12/2007 |
| DE | 2518270 A1 | 3/1976 |

(Continued)

OTHER PUBLICATIONS

International Search Report for Application No. PCT/US2014/028805, dated Jul. 10, 2014, 3 pages.
International Preliminary Report on Patentability for Application No. PCT/US2014/028805, dated Sep. 15, 2015, 7 pages.
Lachman et al. "The Theory and Practice of Industrial Pharmacy" 1986, 3rd Edition.
Diskets Dispersible Tablets, 40 mg Methadone Hydrochloride, Roxane Laboratories.
Handbook of Pharmaceutical Excipients, American Pharmaceuticals Assoc. & The Pharmaceutical Society of GB, 1986, pp. 134-140.
The Merck Index, p. 769.

(Continued)

*Primary Examiner* — Robert A Wax
*Assistant Examiner* — William Craigo
(74) *Attorney, Agent, or Firm* — McCarter & English, LLP; Maria Laccotripe Zacharakis; Maneesh Gulati

(57) ABSTRACT

The present invention is generally directed to an oral pharmaceutical tablet composition comprising a sulfate salt, for example, sodium sulfate, wherein the composition is capable of administration by direct oral ingestion and by disintegration in water prior to oral ingestion. The present invention is further directed to use of such oral pharmaceutical tablet formulations to induce laxation or to treat or prevent constipation.

35 Claims, 1 Drawing Sheet

(56) References Cited

U.S. PATENT DOCUMENTS

| | | |
|---|---|---|
| 8,263,136 B2 | 9/2012 | Caswell |
| 8,679,549 B2 | 3/2014 | Borody et al. |
| 8,753,611 B2 | 6/2014 | Eichman et al. |
| 8,753,618 B2 | 6/2014 | Shaver |
| 8,778,306 B2 | 7/2014 | Bachwich |
| 8,778,907 B2 | 7/2014 | Pavliv et al. |
| 8,999,313 B2 | 4/2015 | Clayton et al. |
| 2004/0115282 A1 | 6/2004 | Keiser et al. |
| 2007/0082061 A1 | 4/2007 | Ayala et al. |
| 2007/0087056 A1 | 4/2007 | Guthmann et al. |
| 2008/0260682 A1 | 10/2008 | Rose et al. |
| 2010/0255122 A1 | 10/2010 | Garren et al. |
| 2010/0297264 A1 | 11/2010 | Kastenberg |
| 2011/0223252 A1 | 9/2011 | Borody et al. |
| 2011/0293747 A1 | 12/2011 | Cleveland |
| 2013/0121916 A1 | 5/2013 | Baroni |
| 2013/0136806 A1 | 5/2013 | Zanarotti et al. |
| 2013/0164384 A1 | 6/2013 | Johnson et al. |
| 2013/0189377 A1 | 7/2013 | Cockett et al. |
| 2013/0225692 A1 | 8/2013 | Stein et al. |
| 2013/0296314 A1 | 11/2013 | Borody et al. |
| 2014/0010895 A1 | 1/2014 | Halphen et al. |
| 2014/0087007 A1 | 3/2014 | Cleveland et al. |
| 2014/0147518 A1 | 5/2014 | Seldon et al. |
| 2014/0235730 A1 | 8/2014 | Subramanian et al. |
| 2014/0255495 A1 | 9/2014 | Bachwich |
| 2015/0056140 A1 | 2/2015 | Borody et al. |

FOREIGN PATENT DOCUMENTS

| | | | |
|---|---|---|---|
| EP | 0049061 A1 | 4/1982 | |
| EP | 0073428 A2 | 3/1983 | |
| EP | 0080862 A1 | 6/1983 | |
| EP | 0159735 A1 | 10/1985 | |
| EP | 0231356 A1 | 8/1987 | |
| EP | 0281200 A1 | 9/1988 | |
| EP | 0670725 A1 | 9/1995 | |
| EP | 0858326 B1 | 4/2003 | |
| EP | 1663257 B1 | 1/2009 | |
| EP | 1499331 B1 | 2/2010 | |
| EP | 1750702 B1 | 8/2010 | |
| EP | 2263680 B1 | 12/2010 | |
| EP | 1742645 B1 | 1/2011 | |
| EP | 2234482 B1 | 2/2011 | |
| EP | 2292244 A2 | 3/2011 | |
| EP | 1976520 B1 | 4/2011 | |
| EP | 2233147 B1 | 10/2011 | |
| EP | 2453873 A1 | 5/2012 | |
| EP | 2544543 A1 | 1/2013 | |
| EP | 2696690 A4 | 10/2014 | |
| EP | 2782581 A1 | 10/2014 | |
| EP | 2862566 A1 | 4/2015 | |
| GB | 2058565 A | 4/1981 | |
| GB | 2172006 A | 9/1986 | |
| WO | WO-8909604 A1 | 10/1989 | |
| WO | WO-0025744 A1 | 5/2000 | |
| WO | WO-03000299 A1 | 1/2003 | |
| WO | WO-03092589 A2 | 11/2003 | |
| WO | WO-2005102364 A1 | 11/2005 | |
| WO | WO-2006118562 A1 | 11/2006 | |
| WO | WO-2007013093 A2 | 2/2007 | |
| WO | WO-2008141368 A1 | 11/2008 | |
| WO | WO-2012013928 A1 | 2/2012 | |
| WO | WO 2012013928 A1 * | 2/2012 | ........... A61K 9/2031 |
| WO | WO-2014032108 A1 | 3/2014 | |
| WO | WO-2014-144407 A1 | 9/2014 | |

OTHER PUBLICATIONS

The United States Pharmacopeia, Twentieth Revision, Official from Jul. 1, 1980; Pharmaceutic Ingredients.

Caramella et al. "The Role of Swelling in the Disintegration Process", Int. J. Pharm. Tech. & Prod. Mfr., 5(2) 1-5, 1984, pp. 1-5.

Pharmaceutical Dosage Forms: Tablets, vol. 1, pp. 122-129.

Nagy et al. "Untersuchungen uber die Texturund die Eigenschaften von Acetylsalicylsaure-Tabletten" Die Pharmazie 33, H. 11, 1978, pp. 747-749.

Martindale, 29$^{th}$ Ed., The Pharmaceutical Press, London, 1989 (HA Liebermann), p. 1435.

The United States Pharmacopoeia, 18$^{th}$ Revision, "Disintegration Test for Uncoated Tablets" Sep. 1, 1970, pp. 932-934.

Chalmers et al. "Oxytetracycline Tablet Formulations: The Influence of Excipients and the Method of Granulation" J. Pharm. Pharmac., 1976, 28, 234-238.

U.S. Appl. No. 62/049,830, filed Sep. 12, 2014.

U.S. Appl. No. 61/552,431, filed Oct. 27, 2011.

U.S. Appl. No. 61/717,599, filed Oct. 23, 2012.

Awada et al., Regarding the Significance of Granulation in Pharmaceutical Products. Powder and Powder Metallurgy. 1964;11(6):29-37.

* cited by examiner

Disintegration Time (min) vs. Sodium Sulfate Particle Size
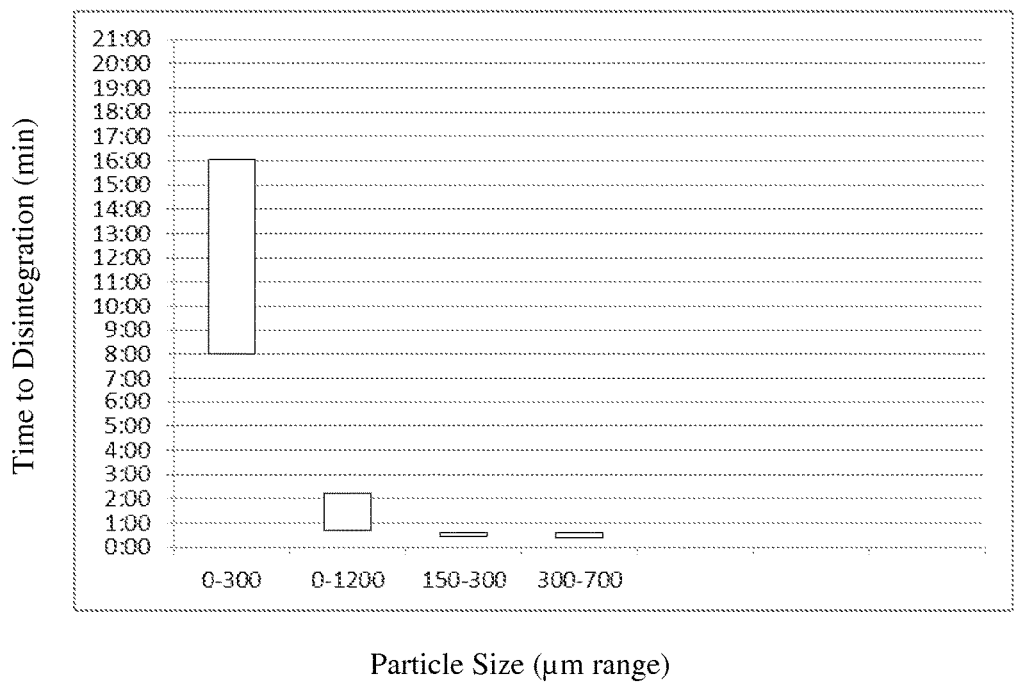

DUAL USE ORAL PHARMACEUTICAL COMPOSITION TABLETS OF SULFATE SALTS AND METHODS OF USE THEREOF

RELATED APPLICATION

This application is a 35 U.S.C. § 371 national stage filing of International Application No. PCT/US2014/028805, filed Mar. 14, 2014, which claims priority to U.S. Provisional Application No. 61/798,759, filed Mar. 15, 2013. The entire contents of each of the foregoing applications are hereby incorporated by reference herein in their entirety.

FIELD OF THE INVENTION

The present invention is generally directed to an oral pharmaceutical tablet composition comprising sulfate salts, wherein the composition is capable of administration by direct oral ingestion similar to a typical immediate release tablet and by rapid disintegration in water prior to oral ingestion.

BACKGROUND

Dosage Forms

Delivery of medication to a patient is often in the form of a tablet, liquid formulation or powder for reconstitution. Each dosage form has disadvantages. Patients are often unwilling, or unable, to swallow tablets, especially when the tablets are relatively large, or when an effective dose requires ingestion of multiple tablets. Challenges associated with swallowing tablets are particularly relevant for children and older adults. Likewise, some patients are unwilling, or unable, to drink liquid pharmaceutical formulations due to an undesirable taste and/or mouth feel.

When the amount of a specific active ingredient to be administered exceeds the amount that can be conveniently formulated in a tablet, the dosage is often provided as a powder or liquid concentrate. The powder or concentrate is then reconstituted for administration as an oral liquid, syrup or powder suspension. The preparation of a liquid formulation from a powder or liquid concentrate can be inconvenient or cumbersome, especially when the patient must take the medication chronically or frequently. This may result in reduced patient compliance and ultimately, in reduced effectiveness of the treatment regimen.

A single dosage form that can be administered as either an immediate release tablet or liquid provides options for patients, caregivers and hospitals when administering a medication to patients who prefer, or are unable, to take one form of medication or the other. For instance, a dual purpose tablet that can be swallowed whole or disintegrated in liquid prior to ingestion would be useful for patients able to swallow tablets, or for patients who prefer or require a medication in a liquid form, or for patients to whom the liquid is directly administered (e.g. delivery through a feeding tube).

Sodium Sulfate

Sodium sulfate is an abundant, naturally occurring salt known to have a laxative effect. However, formulating sodium sulfate in dosage forms, either for direct oral ingestion or in aqueous solution is quite challenging, stemming, at least in part, from the levels of salt required to achieve the desired laxative effect and, further, from the extreme hygroscopic nature and unique solubility profile of sodium sulfate.

With respect to formulating sulfate salts in tablet form for direct oral ingestion, the challenge stems, at least in part, from formulating a convenient dosage form containing a high level and/or effective amount of sodium sulfate to achieve the desired laxative effect. The laxative effect of sulfate salts requires approximately between 2 to 7 grams of sulfate ion and/or 3 to 11 grams of sulfate salts. However, until now, formulating tablets with a high level of sodium sulfate at a size appropriate for direct ingestion while minimizing the number of tablets required to induce laxation has proved challenging.

In addition, the extreme hygroscopic properties of sodium sulfate make the provision of a tablet formulation difficult. When placed in the mouth, the sodium sulfate immediately scavenges all available saliva creating an undesirable mouth feel and dry mouth, thereby making swallowing difficult.

With respect to formulating a tablet dosage form of sodium salt for disintegration in water, the chemical properties of sodium sulfate present significant challenges. Sodium sulfate exhibits unusual water solubility characteristics in that its solubility increases more than 10-fold from 0° C. to 32.384° C. At 32.384° C. the solubility curve changes and crystal water is released and the hydrated salt melts. In contrast to other salts (e.g., potassium, magnesium), the solubility of sodium sulfate does not increase with increasing temperature above 32.384° C. Due to these solubility characteristics, sodium sulfate will crystallize when concentrated and/or cooled.

The reaction of sodium sulfate and water is exothermic, generating heat during hydration and causing the localized water temperature to increase significantly. When sodium sulfate is added to ambient temperature water with no agitation, the water wets the sodium sulfate which is converted to sodium decahydrate and creates an exothermic reaction in the immediate physical area. The exothermic reaction can increase the temperature of the localized wetted salt by as much as 10° C. This results in a portion of the sodium sulfate dissolving to form a localized concentrated solution. However, as the heat from the reaction dissipates into the surrounding solution, the temperature of the localized high concentration sodium sulfate solution decreases and the sodium sulfate recrystallizes forming a very hard mass of sodium sulfate decahydrate (i.e., mirabilite).

Until now, acceptable tablets capable of rapidly disintegrating in water could only be achieved with the inclusion of a high level of inactive ingredients and excipients, which significantly increases the weight and mass of the final dosage formulation and potentially doubles the number of tablets needed to deliver an effective dose. Indeed, formulating tablets of sulfate salts for dispersion in water required about 50% to 90% of excipient, thereby limiting the levels of sulfate salts present therein.

For these reasons, formulation scientists have sought to formulate sulfate salts at the dosage levels necessary to achieve laxation in a powdered form for reconstitution or as a liquid or syrup.

Other forms of tablets include buccal tablets, sublingual tablets, chewable tablets and effervescent tablets. However, these formulations fail to address (i) the need for a versatile and convenient formulation to address patient compliance issues, and (ii) the need for a formulation of a high dose of sodium sulfate to achieve the desired laxative effect.

Dual use tablets of tetracycline have been proposed (see, U.S. Pat. No. 5,211,958; "Pharmaceutical Composition and Process for its Preparation"). However, the unique properties of sodium sulfate as described above do not allow for mere application of the teachings of proposed dual use tablets of alternative active agents to formulating dual use sodium sulfate tablets having a high level of active agent. In addition, the proposed tetracycline tablets include greater than 50% by weight of excipient. Moreover, the tetracycline tablets previously proposed have not been shown to be capable of disintegration in cool or cold water. Typical drinking water sources provide water at temperatures less than 20° C. An acceptable dual use tablet composition should perform as claimed throughout all typical drinking water temperatures.

SUMMARY OF THE INVENTION

The present invention provides a unique and versatile dual use tablet formulation of sulfate salt, for example, sodium sulfate, that is capable of administration by direct oral ingestion or, alternatively, by disintegration in water prior to oral ingestion. Accordingly, the present invention overcomes the challenges of patient compliance and, further, the challenges associated with formulating tablets of sulfate salts.

In one aspect, the present invention provides an oral pharmaceutical tablet composition including at least one sulfate salt, and capable of administration by direct oral ingestion and by disintegration in water prior to oral ingestion. In one embodiment, the composition may include sodium sulfate.

In another embodiment, the oral pharmaceutical tablet composition may disintegrate in water at about 2° C. or greater, for example, about 2° C. to about 15° C., in less than about 150 or about 120 seconds. In various embodiments, the tablet composition may disintegrate in water at about 8° C. or greater, for example, about 8° C. to about 10° C., in less than about 90 seconds, for example, less than 60 seconds. In another embodiment, the composition may disintegrate in water at about 5° C. or greater, for example, about 5° C. to about 10° C., in less than about 120 seconds, for example, less than 90 seconds. In another embodiment, the composition may disintegrate in water at about 2° C. or greater, for example, about 2° C. to about 10° C., in less than about 150 seconds.

In yet another embodiment, the composition of the invention does not disintegrate in the mouth in less than about 30 seconds upon direct oral ingestion. In another embodiment, the composition of the invention does not disintegrate in the mouth in less than about 60 seconds upon direct oral ingestion.

In one aspect, the oral pharmaceutical tablet composition includes sodium sulfate, and the composition is capable of administration by direct oral ingestion and by dissolution in water prior to oral ingestion, wherein the composition disintegrates in water at about 2° C. or greater, for example, about 2° C. to about 15° C., in less than about 120 or about 150 seconds, and the composition does not disintegrate in the mouth in less than about 30 seconds upon direct oral ingestion. In another embodiment, the composition of the invention may include potassium sulfate and/or magnesium sulfate. In yet another embodiment, the composition of the invention includes potassium sulfate.

In another embodiment, the invention includes at least about 60%, 65%, 70%, 75%, 80%, 85% or 90% by weight of a sulfate salt selected from the group consisting of sodium sulfate, potassium sulfate, magnesium sulfate and combinations thereof. In another embodiment, the invention includes at least about 70% by weight of a sulfate salt selected from the group consisting of sodium sulfate, potassium sulfate, magnesium sulfate and combinations thereof. In yet another embodiment, the composition of the invention includes at least about 70% by weight of sodium sulfate and potassium sulfate.

One embodiment of the present invention provides a composition including at least about 40%, 45%, 50%, 55%, 57%, 60% or 65% by weight of sodium sulfate. In another embodiment, the composition includes between about 40% and about 65%, or between about 50% and about 60% by weight of sodium sulfate.

In certain embodiments, the oral pharmaceutical tablet composition of the invention is substantially free of sodium sulfate particles less than about 150 μm, 200 μm, 250 μm or 300 μm and sodium sulfate particles greater than about 700 μm, 750 μm, 800 μm, 900 μm or 1000 μm. For example, the composition may be substantially free of sodium sulfate particles less than about 150 μm and greater than about 700 μm. Further by way of example, the composition may be substantially free of sodium sulfate particles less than about 300 μm and greater than about 700 μm.

In yet another embodiment, at least about 90%, 91%, 92%, 93%, 94%, 95%, 96%, 97%, 98%, or 99% by weight of sodium sulfate in the composition comprises sodium sulfate particles that are greater than about 150 μm, 200 μm, 250 μm or 300 μm and less than about 700 μm, 750 μm, 800 μm, 900 μm or 1000 μm. In another embodiment of the invention, at least about 99% by weight of sodium sulfate in the composition comprises sodium sulfate particles that are greater than about 150 μm, 200 μm, 250 μm or 300 μm and less than about 700 μm, 750 μm, 800 μm, 900 μm or 1000 μm.

In another embodiment, at least about 99% by weight of sodium sulfate in the composition comprises sodium sulfate particles that are greater than about 150 μm and less than about 700 μm. In yet another embodiment, at least about 99% by weight of sodium sulfate in the composition comprises sodium sulfate particles that are greater than about 300 μm and less than about 700 μm.

In a particular embodiment, the oral pharmaceutical tablet composition is between about 1000 mg and about 2500 mg, about 1500 mg and about 2000 mg, or about 1700 mg and about 1900 mg. For example, the composition may be about 1800 mg.

In another embodiment, the composition includes a coating. The coating may be a copolymer of polyvinyl alcohol and polyethylene glycol.

The composition may also include at least one excipient selected from the group consisting of a disintegrant, a binder, a glidant, a lubricant, and combinations thereof. In one embodiment, the total excipient level in the composition is less than about 40%, 35%, 30% or 25% by weight of the composition. For example, the total excipient level in the composition is less than about 30% by weight of the composition.

In another embodiment, the tablet composition includes a disintegrant. The disintegrant may be selected from the group consisting of povidone, Kollidon CL, Kollidon CL-SF, sugar, sucrose, dextrose, mannitol, and a combination thereof. In one embodiment, the disintegrant includes a combination of mannitol and povidone. In another embodiment, the disintegrant includes Kollidon CL and/or Kollidon CL-SF.

In addition, the tablet composition may include a binder. The binder may be selected from the group consisting of polyethylene glycol, PEG3350, PEG8000 and combinations thereof.

In another embodiment, the tablet composition includes a glidant, for example, fumed silica.

In yet another embodiment, the tablet composition includes a lubricant, for example, magnesium stearate, sodium stearyl fumarate, and combinations thereof.

In one aspect, the present invention provides an oral pharmaceutical tablet composition including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, and wherein the tablet comprises a coating.

In another aspect, the present invention provides an oral pharmaceutical tablet composition including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition comprises at least about 70% by weight of sodium sulfate and potassium sulfate, and wherein the tablet comprises a coating.

In another aspect of the invention, the present invention provides an oral pharmaceutical tablet composition including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition is substantially free of sodium sulfate particles less than about 150 µm and greater than about 700 µm, and wherein the tablet comprises a coating.

In another aspect of the invention, the present invention provides an oral pharmaceutical tablet composition including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition is substantially free of sodium sulfate particles less than about 150 µm and greater than about 700 µm, and wherein the tablet comprises a coating and a disintegrant.

In another aspect, the invention provides a method of preparing the oral pharmaceutical tablet composition including the steps of blending at least one sulfate salt and at least one excipient and compressing the resulting blend into a tablet. The step of blending may include blending a batch of sodium sulfate, wherein the batch of sodium sulfate is substantially free of sodium sulfate particles less than about 150 µm and greater than about 750 µm, for example, less than about 300 µm and greater than about 750 µm, less than about 150 µm and greater than about 1000 µm, or less than about 300 µm and greater than about 1000 µm.

In another embodiment, the invention provides a method of preparing the oral pharmaceutical tablet composition including the steps of blending a batch of sodium sulfate and at least one excipient, wherein the batch of sodium sulfate is substantially free of sodium sulfate particles less than about 150 µm and greater than about 700 µm, for example, less than about 300 µm and greater than about 750 µm, less than about 150 µm and greater than about 1000 µm, or less than about 300 µm and greater than about 1000 µm, and compressing the resulting blend into a tablet.

The method may further include coating the tablet. In another embodiment, the method of the invention includes substantially removing sodium sulfate particles less than about 150 µm and greater than about 700 µm, for example, less than about 300 µm and greater than about 750 µm, less than about 150 µm and greater than about 1000 µm, or less than about 300 µm and greater than about 1000 µm, prior to blending. In yet another embodiment, the excipient is selected from the group consisting of a disintegrant, a binder, a glidant, a lubricant, and combinations thereof.

In a further aspect, the invention includes a method for inducing laxation in a subject including administering to the subject at least one oral pharmaceutical tablet composition of the invention, thereby inducing laxation. In yet another aspect, the invention includes a method for preventing or treating constipation in a subject, the method including administering to the subject at least one oral pharmaceutical tablet composition of the invention, thereby treating or preventing constipation.

In one embodiment of the foregoing methods of the invention, the composition is swallowed directly by the subject. In another embodiment, the step of administering the composition comprises orally ingesting an aqueous dispersion of the composition. In yet another embodiment of the method of the invention, laxation is induced without inducing a clinically significant electrolyte shift in the subject. In yet another aspect of the method of the invention, the method treats or prevents constipation without inducing a clinically significant electrolyte shift in the subject. In yet another method of the invention, the subject is administered 2, 3, 4 or 5 oral pharmaceutical tablet compositions.

BRIEF DESCRIPTION OF DRAWINGS

FIG. 1 graphically depicts the effect of sodium sulfate particle size on the disintegration time of sodium sulfate tablets in water, as described in Example 1.

DETAILED DESCRIPTION OF THE INVENTION

The present invention provides a unique dual use tablet formulation comprising sulfate salts, for example, sodium sulfate, that is capable of administration by direct oral ingestion or, alternatively, by disintegration in water prior to oral ingestion. In a particular aspect, the invention is directed to an oral pharmaceutical tablet composition including a sulfate salt, for example, sodium sulfate and, optionally, potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds; in water at about 8° C. or greater, for example, about 8° C. to about 10° C., in less than about 90 seconds, for example, less than 60 seconds; in water at about 5° C. or greater, for example, about 5° C. to about 10° C., in less than about 120 seconds, for example, less than 90 seconds; and/or in water at about 2° C. or greater, for example, about 2° C. to about 10° C., in less than about 120 or about 150 seconds;

and wherein the composition does not disintegrate in the mouth in less than about 30 seconds upon direct oral ingestion.

The pharmaceutical compositions of the present invention overcome challenges of patient compliance by providing a versatile composition that can be taken in a form convenient to the patient. In addition, the pharmaceutical compositions of the present invention overcome the challenges of patient compliance arising from the extreme hygroscopic properties of sodium sulfate, in part, by providing a tablet that can either be disintegrated in water or alternatively, can be ingested directly without scavenging all available saliva so as to cause an undesirable mouth feel, dry mouth and difficulty swallowing.

Moreover, the pharmaceutical compositions of the present invention overcome challenges in formulating high dosage forms of sodium sulfate, as required to achieve a laxative effect. Indeed, the compositions of the present invention allow for incorporation of sulfate salts, including, for example, sodium sulfate and potassium sulfate, at a level of at least about 40%, 45%, 50%, 55%, 60%, 65%, 70%, 75%, 80%, 85% or 90% by weight of the composition and, in particular, incorporation of sodium sulfate at a level of at least about 40%, 45%, 50%, 55%, 57%, 60% or 65% by weight of the composition. By minimizing the levels of inactive agents, e.g., excipients, and maximizing the levels of sulfate salts and, in particular, sodium sulfate salt, the oral pharmaceutical compositions of the present invention provide a high dosage form in a convenient tablet form to achieve the desired laxative effect upon administration to the subject. Accordingly, subjects may require ingestion of only 1, 2, 3, 4 or 5 tablets to induce laxation.

Moreover, the pharmaceutical compositions of the present invention overcome the challenges in formulating a tablet form of sodium sulfate that readily and rapidly disintegrates in water or an aqueous solution. The chemical properties and, in particular, the solubility curve, of sodium sulfate often result in recrystallization and formation of a hard mass upon immersion in water, thereby undermining the ultimate goal of providing an aqueous dispersion for ingestion. As used herein, the terms "disintegration" or "disintegrate," in the context of disintegrating in water or an aqueous solution, refer to rupture and/or breaking down of the tablet composition, e.g., disintegration of greater than about 50%, 55%, 60%, 65%, 70%, 75%%, 80%, 85%, 90% or 95% of the composition. In a particular embodiment, the level of disintegration in the context of disintegrating in water or an aqueous solution may be assessed by the methods described in Examples 6 and 7 herein.

Without wishing to be bound by any particular theory, the present inventors have identified that, in part, by removing sodium sulfate particles less than about 150 µm, for example, less than about 300 µm, and, further, by removing sodium sulfate particles greater than about 1000 µm, for example, greater than about 750 µm, tablet formulations of sodium sulfate may be prepared that allow for rapid disintegration in water at about 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C., for example, in under about 150, 120, 90, 60, 45 or 30 seconds. In one embodiment, the tablet disintegrates in water at about 15° C. in less than about 45 seconds. Alternatively or in addition, the tablet may disintegrate in water at about 10° C. in less than about 60 seconds, for example, less than 45 seconds. Alternatively or in addition, the tablet may disintegrate in water at about 8° C. in less than about 90 seconds, for example, less than 60 seconds. Alternatively or in addition, the tablet disintegrates in water at about 5° C. in less than about 120 seconds, for example, less than 90 seconds. Alternatively or in addition, the tablet disintegrates in water at about 2° C. in less than about 120 or about 150 seconds. In various other embodiments, the composition disintegrates in water at about 2° C. or greater, for example, about 2° C. to about 15° C., in less than about 120 or about 150 seconds; in water at about 8° C. or greater, for example, about 8° C. to about 10° C., in less than about 90 seconds, for example, less than 60 seconds; in water at about 5° C. or greater, for example, about 5° C. to about 10° C., in less than about 120 seconds, for example, less than 90 seconds; and/or in water at about 2° C. or greater, for example, about 2° C. to about 10° C., in less than about 120 or about 150 seconds. Accordingly, the tablets possess further versatility in exhibiting a desired disintegration profile in water at room temperature, in cool water and in cold water. As such, the tablets are appropriate for use in regions where available water, e.g., tap water, is colder than room temperature. Indeed, the inventors have identified that sodium sulfate particles greater than about 150 µm, for example, greater than about 300 µm, when compressed into a tablet and combined with the appropriate excipients quickly dissolve in cool water, or in cold water, and further do not recrystallize into a solid mass when immersed therein.

Moreover, the pharmaceutical compositions of the present invention overcome the challenges in formulating a tablet form of sodium sulfate that is resistant to disintegration upon direct oral administration and interaction with saliva. Indeed, the oral pharmaceutical tablet compositions do not disintegrate in the mouth in less than about 90, 75, 60, 45, or 30 seconds upon direct oral ingestion and interaction with saliva. As used herein, the terms "disintegration" or "disintegrate," in the context of disintegration in the mouth of a subject (i.e., upon exposure to the saliva of a subject), refer to erosion of a substantial portion of the tablet composition, e.g., greater than about 90%, 91%, 92%, 93%, 94%, 95%, 96%, 97%, 98% or 99% of the composition. While it is envisioned that a minor degree of erosion may occur when placed in the mouth for direct oral ingestion, as used herein, the terms "disintegration" or "disintegrate" as used in the context of direct oral ingestion requires erosion of a substantial portion of the tablet. In a particular embodiment, the level of disintegration in the context of direct oral ingestion may be assessed by the methods described in Example 2 herein.

The inventors have further identified that by removing sodium sulfate particles less than about 150 µm, preferably, less than about 300 µm, denser and thinner tablets were able to be generated. Moreover, by removing sodium sulfate particles greater than about 1000 µm, preferably, greater than about 750 µm, tablet weight variation was minimized during the manufacturing process.

In addition, because the oral pharmaceutical compositions of the present invention are in tablet form, the compositions provide a commercial benefit for purposes of storage and transportation by avoiding the need for inclusion of preservatives.

Accordingly, the present inventors have identified a unique, versatile and efficacious formulation of sulfate salts, for example, sodium sulfate.

Pharmaceutical Compositions

In one aspect, the present invention provides an oral pharmaceutical tablet composition comprising a sulfate salt, for example, sodium sulfate, wherein the composition is capable of administration by direct oral ingestion and by disintegration in water prior to oral ingestion. In another aspect, the present invention provides an oral pharmaceutical tablet composition, including sodium sulfate, wherein the composition is capable of administration both by direct oral ingestion and by disintegration in water prior to oral ingestion, wherein the composition disintegrates in water at about 2° C. or greater, for example, about 2° C. to about 15° C., in less than about 120 or about 150 seconds, and wherein the composition does not disintegrate in the mouth in less than about 30 seconds upon direct oral ingestion. In yet another aspect, the present invention provides an oral pharmaceutical tablet composition including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, and wherein the tablet includes a coating. In yet another aspect, the present invention provides an oral pharmaceutical tablet composition, including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition comprises at least about 70% by weight of sodium sulfate and potassium sulfate, and wherein the tablet comprises a coating. In a further aspect, the invention provides an oral pharmaceutical tablet composition, including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition is substantially free of sodium sulfate particles less than about 150 µm and greater than about 700 µm, and wherein the tablet further includes a coating and a disintegrant. In yet another embodiment, the invention provides an oral pharmaceutical tablet composition, including sodium sulfate and potassium sulfate, wherein the composition is capable of administration by direct oral ingestion and by disintegration in water prior to oral ingestion, wherein the composition disintegrates in water at about 2° C. or greater, for example, about 2° C. to about 15° C., in less than about 120 or about 150 seconds, wherein the composition does not disintegrate in the mouth in less than about 30 seconds upon direct oral ingestion, wherein the composition is substantially free of sodium sulfate particles less than about 150 µm and greater than about 700 µm, and wherein the tablet includes a coating.

Sulfate Salts

As used herein, the term "sulfate salt" refers to combinations of sulfate ion, i.e., $SO_4^{2-}$, and an appropriate cation. Non-limiting examples of sulfate salts for use in the present invention include, for example, sodium sulfate ($Na_2SO_4$), magnesium sulfate ($MgSO_4$), potassium sulfate ($K_2SO_4$) and combinations thereof.

In certain embodiments, the oral pharmaceutical tablet compositions of the invention include sodium sulfate. The sodium sulfate may be in the form of an anhydrous powder (e.g., Thenardite) or in the form of a decahydrate (e.g., Glauber's salt, mirabilite). In certain embodiments, the oral pharmaceutical tablet composition includes sodium sulfate and at least one other sulfate salt, for example, magnesium sulfate or potassium sulfate. For example, in one embodiment, the oral pharmaceutical tablet composition includes sodium sulfate and potassium sulfate. In yet another embodiment, the invention includes sodium sulfate, potassium sulfate and magnesium sulfate.

Sulfates are known to exhibit laxative effect. Prior sulfate compositions included only a small quantity of active ingredient, generally less than 30% by weight of the tablet, as a large quantity of inactive agents were required to achieve disintegration. By increasing the level of sulfate, the tablets of the present invention serve to minimize the number and size of tablets needed to achieve a desired therapeutic effect. In certain embodiments, the oral pharmaceutical tablet composition includes at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% by weight of sulfate salts as the active ingredient.

In certain embodiments of the invention, the oral pharmaceutical tablet composition includes at least about 70% by weight of a sulfate salt selected from the group consisting of sodium sulfate, potassium sulfate, magnesium sulfate and combinations thereof. In a further embodiment, the oral pharmaceutical tablet composition includes at least about 70% by weight of sodium sulfate and potassium sulfate. In certain embodiments, the oral pharmaceutical tablet composition comprises at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% by weight of sodium sulfate. In yet another embodiment, the oral pharmaceutical tablet composition comprises between about 40% and about 65% or between about 50% and about 60% by weight of sodium sulfate.

Approximately 90% of the sodium sulfate particles found in commercially available sodium sulfate are less than about 300 µm in size, according to USP standards. This sodium sulfate powder forms slow dissolving crystals when added to water. However, removal of particles less than 150 µm in size results in a powder which may be used to form a tablet which dissolves rapidly (e.g., about 30, 60 or 90 seconds) in water, for example, at about 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C. In addition, removal of particles of larger size, for example, greater than about 1000 µm, results in a denser powder with a reduced void fraction. As a result, a denser and thinner tablet can be produced.

Accordingly, in certain embodiments, the oral pharmaceutical tablet composition is substantially free of sodium sulfate particles less than about 150 µm, 200 µm, 250 µm, or 300 µm and sodium sulfate particles greater than about 700 µm, 750 µm, 800 µm, 900 µm, or 1000 µm. In another embodiment, the composition is substantially free of sodium sulfate particles less than about 300 µm and greater than about 700 µm. In another embodiment, the composition is substantially free of sodium sulfate particles less than about 150 µm and greater than about 700 µm. As used herein, the term "substantially free" refers to a composition including an insignificant level of particles falling outside the desired range of particle sizes, for example, less than about 5%, 4%, 3%, 2%, 1%, 0.5%, 0.4%, 0.3%, 0.2%, 0.1%, 0.05%, 0.04%, 0.03%, 0.02%, 0.01% by weight of sodium sulfate in the composition. Use of a batch of sodium sulfate particles obtained by use of standard techniques known in the art to obtain a desired range of particle sizes, for example, including use of appropriate sieves, meshes or other techniques described herein or known in the art, renders the resulting composition "substantially free" of particles falling outside the desired range of particle sizes for purposes of the present invention.

Reference herein to the size of particles is in accordance with the state of the art. For example, reference to size can refer to particles obtained upon use of an appropriate sieve, e.g., air sieving or laboratory sieving, or mesh.

The oral pharmaceutical tablet composition may include sodium sulfate wherein at least about 90%, 91%, 92%, 93%, 94%, 95%, 96%, 97%, 98% or 99% by weight of the sodium sulfate is formed of sodium sulfate particles that are greater than about 150 μm, 200 μm, 250 μm, or 300 μm but less than about 700 μm, 750 μm, 800 μm, 900 μm, or 1000 μm. More specifically, the oral pharmaceutical tablet composition may include sodium sulfate wherein at least about 99% by weight of the sodium sulfate is formed of sodium sulfate particles that are greater than about 150 μm, 200 μm, 250 μm or 300 μm and less than about 700 μm, 750 μm, 800 μm, 900 μm or 1000 μm. In another embodiment of the invention, the oral pharmaceutical tablet composition may include sodium sulfate wherein at least about 99% by weight of the sodium sulfate is formed of sodium sulfate particles that are greater than about 150 μm and less than about 700 μm. In yet another embodiment of the invention, the oral pharmaceutical tablet composition may include sodium sulfate wherein at least about 99% by weight of the sodium sulfate is formed of sodium sulfate particles that are greater than about 300 μm and less than about 700 μm.

Coatings

In various embodiments, the present invention includes a coating. As used herein, the term "coating" refers to an agent that protects the active ingredients of a pharmaceutical composition from deteriorating through contact with air, moisture or saliva, masks unpalatable tasting compounds, or affects the rate or location of the release of an active ingredient. The coating further provides protection to the tablet during oral administration but also disintegrates rapidly in water to allow for disintegration of the tablet and subsequent ingestion of the resulting aqueous dispersion. In fact, the present inventors surprisingly found that the coatings did not substantially increase disintegration time in water.

Although an uncoated tablet is already amenable to direct ingestion, typical of an immediate release tablet, the addition of a coating can serve to render the sulfate salts more palatable. Sulfate salts are extremely hygroscopic and when taken orally, the tablet immediately scavenges all available saliva from the mouth creating an undesirable mouth feel, dry mouth, and difficulty swallowing. Coated tablets further contribute to the ability of the tablets to withstand disintegration upon contact with saliva and, further, to avoid patient detection of the objectional taste of sulfates, when placed directly in the mouth, for example, for at least about 30, 60 or 90 seconds. For the foregoing reasons, the coating preferably does not dissolve and rupture as quickly in saliva, as compared to water.

Non-limiting examples of coatings for use in the present invention include hydroxypropylmethyl cellulose, methylcellulose, hydroxypropylcellulose, carboxymethylcellulose sodium, polyethylene glycols, synthetic polymers, shellac, corn protein zein, polysaccharides, polyvinyl alcohol, polyethylene glycol, Kollicoat IR (polyvinyl alcohol-polyethylene glycol co-polymer), Kollicoat SR 30D (Polyvinyl acetate stabilized with polyvinylpyrrolidone and sodium lauryl sulfate) or gelatin. In one embodiment, the coating is soluble. In various embodiments, the coating is selected from the group consisting of hydroxypropylmethyl cellulose, methylcellulose, hydroxypropylcellulose, carboxymethylcellulose sodium, polyethylene glycols, and a copolymer of polyvinyl alcohol and polyethylene glycol. In one embodiment, the coating comprises a copolymer of polyvinyl alcohol and polyethylene glycol. This coating is readily soluble and can be used to spray coat the tablets at concentrations up to 30% by weight of the composition. The polyvinyl alcohol and polyethylene glycol form a flexible coating with low tack eliminating the need for plasticizers and detackifiers. In another embodiment, the coating is present at about 1.75% to about 6% or about 2% to about 6% by weight of the composition. As set forth in Example 2 below, tablets with a coating of about 2% by weight of the composition rupture and begin to disintegrate instantly (i.e., within 5 to 10 seconds) when added to water. Tablets with a coating of about 6% by weight of the composition rupture and begin disintegrating in water in up to 30 seconds.

Excipients

The pharmaceutical compositions of the present invention further include at least one excipient. As used herein, the term "excipient" refers to pharmacologically inactive substances that may be used, for example, to increase the volume or mass of a formulation, facilitate the manufacturing process, stabilize or protect active ingredients during storage, affect the solubility of the composition, affect the disintegration of the composition or improve palatability. Non-limiting examples of excipients for use in the present invention include anti-adherents, binders, coatings, disintegrants, fillers, flavors, colors, lubricants, glidants, sorbents, preservatives, and sweeteners. In certain embodiments, the tablets do not include a preservative.

In one embodiment, the oral pharmaceutical tablet composition comprises at least one excipient selected from the group consisting of a disintegrant, a binder, a glidant, a lubricant, and combinations thereof. In particular embodiments, the excipient(s) is soluble. In certain embodiments, the total excipient level in the composition is less than about 40%, 35%, 30%, 25% or 20% by weight of the composition. In one embodiment, the total excipient level in the composition is less than about 30% by weight of the composition. In a particular embodiment, the total excipient level in the composition is less than about 25% by weight of the composition.

Disintegrants

In one embodiment, the oral pharmaceutical tablet composition comprises a disintegrant. As used herein, the term "disintegrant" refers to a compound that expands and dissolves when wet, causing tablets to break apart and release the active agent, e.g., sulfate salts, at the desired site of absorption. The disintegrant also functions to ensure that the compounds are in contact with the solvent, such as water, in order to cause disintegration.

Non-limiting examples of disintegrants for use in the present invention include agar, calcium carbonate, potato and tapioca starch, alginic acid, certain silicates, colloidal silicon dioxide, sodium starch glycolate, crospovidone, crosslinked polyvinylpyrrolidone, povidone, Kollidon CL, Kollidon CL-SF, sugar, sucrose, dextrose, mannitol, Ludiflash (90% mannitol, 5% crospovidone (Kollidon 30) and 5% polyvinylacetate (Kollicoat SR 30D) sodium carbonate, and combinations thereof. In one embodiment, the disintegrant(s) is soluble. In one embodiment, the disintegrant is selected from the group consisting of povidone, Kollidon CL, Kollidon CL-SF, sugar, sucrose, dextrose, mannitol, or a combination thereof. In one embodiment, the oral pharmaceutical tablet compositions of the invention include mannitol and, optionally, an additional disintegrant. For example, the disintegrant may be a combination of a sugar and povidone. In a particular embodiment, the disintegrant is a combination of mannitol and povidone. In a particular embodiment, the disintegrant is a combination of mannitol, Kollidon CL and Kollidon CL-SF. The combination of mannitol and povidone exhibits a particularly desired disintegration profile. Without wishing to be bound to a particular theory, it is believed that mannitol draws water into the interior of the tablet, making the water available to other disintegrants, such as povidone, thereby allowing the disintegrant to swell at a faster rate. The ratio of a wicking agent, such as mannitol, and a disintegrant, such as povidone, can serve to effect a desired rate of disintegration. In particular embodiments, the mannitol is present at about 6% to about 15%, or at about 8% to about 12% by weight of the composition. Alternatively or in addition, the Kollidon CL is present at about 4% to about 12%, or at about 6% to about 10% by weight of the composition. Alternatively or in addition, the Kollidon CL-SF is present at about 2% to about 7%, or about 3% to about 6% by weight of the composition.

Binders

In one embodiment, the oral pharmaceutical tablet composition includes a binder. As used herein, the term "binder" refers to an inactive ingredient that holds the composition together when the ingredients are compressed to make the tablet. Non-limiting examples of binders for use in the present invention include sucrose, lactose, starches, cellulose, modified cellulose such as microcrystalline cellulose and hydroxypropyl cellulose, xylitol, sorbitol, malitol, gelatin, polyvinylpyrrolidone, polyethylene glycol, PEG3350, PEG8000, xanthan gum and combinations thereof. In one embodiment, the binder is selected from the group consisting of polyethylene glycol, PEG3350, PEG8000 and combinations thereof. PEG3350 and PEG8000 are particularly advantageous as binders because they are fully soluble and allow for the production of a well formed tablet. In yet another embodiment, the binder is present at about 1% to about 10%, at about 2% to about 6%, or at about 3% to about 5% by weight of the composition.

Glidant

In one embodiment, the oral pharmaceutical tablet composition includes a glidant. As used herein, the term "glidant" refers to an inactive ingredient used as a flow aid during the production of the tablet so as to allow the ingredients to blend homogenously and to aid in compression. Non-limiting examples of glidants for use in the present invention include fumed silica (Aerosil 200), talc, magnesium carbonate, and combinations thereof. In one embodiment of the oral pharmaceutical tablet composition, the glidant is fumed silica. In yet another embodiment, the glidant is present at less than about 2% or about 1%. Alternatively, or in addition, the glidant is present at between about 0.1% and about 0.8% or between about 0.2% to about 0.5% by weight of the composition.

Lubricant

In one embodiment, the oral pharmaceutical tablet composition includes a lubricant. As used herein, the term "lubricant" refers to an inactive ingredient which facilitates compression of the composition to form a tablet and release of the tablet from the mold during the manufacturing process. Non-limiting examples of lubricants for use in the present invention include magnesium stearate, stearic acid, sodium stearyl fumarate, hydrogenated vegetable oil, talc, silica, mineral oil, glycerol monostearate, and combinations thereof. In one embodiment, the oral pharmaceutical tablet composition includes a lubricant selected from the group consisting of mineral oil, glycerol monostearate, magnesium stearate, sodium stearyl fumarate, and combinations thereof. In certain embodiments, the oral pharmaceutical tablet composition includes a lubricant which is present at less than about 2%, 1% or 0.5%. Alternatively, or in addition, the lubricant is present at between about 0.2% and about 0.8% or between about 0.4% and about 0.6% by weight of the composition.

Tablet

The oral pharmaceutical compositions of the invention are provided in the form of a tablet. The tablet compositions of the present invention are designed so as to maximize the sulfate content and to minimize the number of tablets required, both to induce the desired laxative effect and, further to address patient compliance and convenience issues. Accordingly, in one embodiment, the oral pharmaceutical tablet composition is between about 1000 mg and about 3000 mg, between about 1500 mg and about 2500 mg, or about 1700 mg and about 2000 mg. In a particular embodiment, the oral pharmaceutical tablet composition may be about 1800 mg.

In a preferred embodiment, the tablets have a hardness between about 7 kp to about 15 kp, about 7 kp to about 12 kp, about 8 kp to about 12 kp or about 10 kp to about 15 kp. The tablet should be of sufficient hardness to allow for coating thereof and to allow for convenient manufacturing thereof, but not too hard so as to impede the desired disintegration profile in water.

The tablet may be of any shape. In one embodiment, the tablet is an oblong, biconvex tablet, for example, of about 1800 mg, with flat sides, optionally produced using standard compression tooling. This shape and size is convenient for patients because the oval shape with rounded faces provides for better oral administration.

The tablets of the invention may be made by any of a variety of standard techniques in the art including, for example, extrusion, spheronization, wet-granulation, milling and direct compression, as appropriate.

In one aspect, the invention provides a method of preparing the oral pharmaceutical tablet composition including the steps of blending at least one sulfate salt and at least one excipient and compressing the resulting blend into a tablet. The step of blending may include blending a batch of sodium sulfate, wherein the batch of sodium sulfate is substantially free of sodium sulfate particles less than about 150 μm and greater than about 750 μm, for example, less than about 300 μm and greater than about 750 μm, less than about 150 μm and greater than about 1000 μm, or less than about 300 μm and greater than about 1000 μm.

In another embodiment, the invention provides a method of preparing the oral pharmaceutical tablet composition including the steps of blending a batch of sodium sulfate and at least one excipient, wherein the batch of sodium sulfate is substantially free of sodium sulfate particles less than about 150 μm and greater than about 700 μm, for example, less than about 300 μm and greater than about 750 μm, less than about 150 μm and greater than about 1000 μm, or less than about 300 μm and greater than about 1000 μm, and compressing the resulting blend into a tablet.

The method may further include coating the tablet. In another embodiment, the method of the invention includes substantially removing sodium sulfate particles less than about 150 µm and greater than about 700 µm, for example, less than about 300 µm and greater than about 750 µm, less than about 150 µm and greater than about 1000 µm, or less than about 300 µm and greater than about 1000 µm, prior to blending. In yet another embodiment, the excipient is selected from the group consisting of a disintegrant, a binder, a glidant, a lubricant, and combinations thereof.

In a particular embodiment, the tablets of the invention are made as described in Example 4.

Methods of Treatment

The present invention further provides methods to induce laxation or to treat or prevent constipation by administering the oral tablet pharmaceutical compositions disclosed herein.

The terms "treat" or "treating," as used herein, refer to partially or completely alleviating, inhibiting, delaying onset of, reducing the incidence of, ameliorating and/or relieving constipation, or one or more symptoms of constipation, in one example, symptoms of opioid constipation.

As used herein, the term "subject" means a mammal and includes human and animal subjects, such as domesticated animals (e.g., horses, dogs, cats, etc.) and experimental animals (e.g., mice, rats, dogs, chimpanzees, apes, etc.). In a particular embodiment, the subject is human.

As used herein, the terms "suffer" or "suffering" refers to one or more conditions that a patient has been diagnosed with, or is suspected to have, in particular, constipation.

As used herein, the term "constipation" refers to a condition in which a subject suffers from infrequent bowel movements or bowel movements that are painful and/or hard to pass. A subject experiencing constipation often suffers from straining during bowel movements and/or a sensation of incomplete evacuation following bowel movements.

As used herein, the terms "laxation" or "laxative response" refers to the passage and evacuation of feces.

In one embodiment, the present invention provides methods to induce laxation or to treat or prevent constipation by direct oral ingestion, i.e., swallowing, of the compositions of the invention. In a particular embodiment, the compositions of the invention may be directly ingested with water.

In another embodiment, the compositions of the invention may be disintegrated in water and the subsequent aqueous dispersion ingested orally. While the compositions of the invention are capable of immediate disintegration in cold water, for example, water at between 2° C. and about 10° C., the compositions may be disintegrated in water at varying temperatures. Indeed, the discovery of sodium sulfate oral tablet compositions uniquely capable of disintegration at reduced temperatures of water is not intended to restrict the temperature of water in which the composition is immersed for oral ingestion. For example, the compositions of the invention may be disintegrated in water at 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C. In various embodiments, the compositions of the invention may be disintegrated in 5 ml, 6 ml, 7 ml, 8 ml, 9 ml, 10 ml, 11 ml, 12 ml, 13 ml, 14 ml or 15 ml of water. Alternatively, the compositions of the invention may be administered as an aqueous solution delivered through a feeding tube.

In alternative embodiments, the compositions of the invention may be disintegrated in other aqueous fluids, for example, flavored drinks, and the subsequent aqueous dispersion ingested orally. For purposes of the present invention, saliva and components thereof are not considered an aqueous fluid for rapid disintegration of the composition.

According to the methods described herein, the subjects are administered an effective amount of the sulfate salt tablet to induce laxation. As used herein, an "effective amount" refers to the level required to induce laxation or to treat or prevent one or more symptoms of constipation. In some embodiments, an "effective amount" is at least a minimal amount of the oral sulfate compositions of the invention, which is sufficient for inducing laxation or for treating or preventing constipation. In some embodiments, the term "effective amount," as used in connection with an amount of sulfate ion or sulfate salt(s), refers to an amount of sulfate ion or sulfate salt(s), or compositions thereof sufficient to induce laxation or for treating or preventing constipation.

In various embodiments, the compositions of the invention should be administered so as to result in ingestion of at least 2 grams, 3 grams, 4 grams, 5 grams, 6 grams, 7 grams, 8 grams, 9 grams or 10 grams of sulfate ion, for example, present as sodium sulfate, potassium sulfate or a combination thereof. In various embodiments, the compositions of the invention should be administered so as to result in ingestion of between about 2 grams and about 10 grams, between about 2 grams and 7 grams, between about 3 grams and about 6 grams, or between about 4 grams and about 5 grams of sulfate ion for example, sodium sulfate, potassium sulfate or a combination thereof, to induce laxation or treat or prevent constipation. In other embodiments, the compositions of the invention should be administered so as to result in ingestion of at least 2 grams, 3 grams, 4 grams, 5 grams, 6 grams, 7 grams, 8 grams, 9 grams, 10 grams, 11 grams, 12 grams, 13 grams, 14 grams or 15 grams of sulfate salts, for example, sodium sulfate, potassium sulfate or a combination thereof. In further embodiments, the compositions of the invention should be administered so as to result in ingestion of between about 2 grams and about 15 grams, between about 3 grams and about 11 grams, between about 5 grams and about 9 grams, or between about 6 grams and about 8 grams of sulfate salts, for example, sodium sulfate, potassium sulfate or a combination thereof, to induce laxation or treat or prevent constipation.

To achieve the desired efficacious levels of laxation, the subject may be administered more than one tablet, depending on the composition of the tablet. For example, the subject may be administered 1, 2, 3, 4, 5, 6 or more tablets to induce laxation.

In various embodiments, the methods of the invention result in immediate laxative response. For example, the compositions may induce laxation, e.g., induce a bowel movement, in less than 1 hour, 2 hours, 3 hours, 4 hours, 5 hours or 6 hours.

The pharmaceutical compositions of the invention may be taken as necessary by the subject. For example, the pharmaceutical compositions of the invention may be taken on demand to induce an immediate and desired laxative response. Alternatively, the pharmaceutical compositions may be taken on a regular dosing regimen, for example, three times a day, twice a day or once a day. Such regimens may be for at least one week, two weeks, three weeks, 4 weeks, 5 weeks, 6 weeks, 7 weeks, 8 weeks, or more.

According to the invention, administration of the oral sulfate salt compositions of the invention, either by direct ingestion of the tablet or an aqueous dispersion thereof, induces laxation to treat or prevent constipation without producing clinically significant electrolyte shifts in the subject. The term "clinically significant" as used herein is meant to convey alterations in blood chemistry that are outside the normal upper or lower limits of their normal range or other untoward effects. Clinically significant electrolyte imbalances can be caused by undesirable net water or electrolyte secretion or absorption resulting, for example, in electrolyte balance including: hyperphosphatemia, hypocalcemia, positive sodium balance, and negative potassium balance. Accordingly, in a particular embodiment, the oral sulfate salt compositions of the invention induce laxation and/or treat or prevent constipation without clinically significant alternation of sodium, chloride, bicarbonate, potassium, calcium, and phosphate level and balance or other untoward effects on the recipient.

The effect of the compositions of the invention on electrolyte balance can be assessed by the methods described in U.S. Pat. No. 6,946,149 (Cleveland), issued Sep. 20, 2005, the entire contents of which are hereby incorporated by reference herein.

This invention is further illustrated by the following examples which should not be construed as limiting. The contents of all references, patents and published patent applications cited throughout this application, as well as the figures, are incorporated herein by reference.

EXEMPLIFICATION

Example 1: Effect of Sodium Sulfate Particle Size on Tablet Disintegration in Water We discovered that larger particles of sodium sulfate when added to cold water do not exhibit the same behavior as the fine powder. Removal of the fine particles of sodium sulfate, below about 300 μm, resulted in a form of sodium sulfate powder that would not recrystallize into a solid mass when added to cold water without agitation. When applied to the tablet formulations, several advantages were revealed. Primarily, the tablet disintegration time was greatly reduced. FIG. 1 shows the effects of tablets prepared with sodium sulfate at various ranges of particle sizes.

Preparing tablets with all fines results in a tablet that completely fuses taking 8-16 minutes to disintegrate. Tablets with a wide range of particle sizes, including some fines, still experience a degree of fusing of the particles and an increase in the overall disintegration time. Finally, particle sizes between 150-700 μm result in a tablet that swells and disintegrates in under 90 seconds.

Other advantages were gained with this discovery. Fine powders have low bulk densities. Sodium sulfate powder does not flow well and requires higher levels of flow aid (fumed silica) to achieve a blend that flows well and can be compressed with minimal variations in tablet weight and thickness. By increasing the particle size of the sodium sulfate, the bulk density was increased and the flow properties greatly improved allowing a reduction in the levels of binder and flow aid. Increasing the bulk density provided a denser tablet blend and ultimately a significant reduction in the tablet thickness.

Example 2: Coatings

As a dual purpose administration form, the tablet is required to disintegrate immediately in water yet be sufficiently protected to survive oral administration without rapidly disintegrating in the oral cavity.

A copolymer of polyvinyl alcohol and polyethylene glycol was tested as a coating material. A coating level of 2% weight gain resulted in a tablet that ruptured and began disintegrating instantly when added to water (5 to 10 seconds) with heavier coated tablets (6% weight gain) taking up to 30 seconds.

During the development of the coating, it was discovered that the coating did not rupture and dissolve as quickly when coated with saliva. The coated tablets could be held for as long as 30-60 seconds in the oral cavity before an objectionable taste from the sulfates could be detected.

We considered whether a component of saliva was slowing the rupturing and swelling of the tablet. Mucin had been identified as the primary thickening and barrier-creating agent present in saliva. To test whether mucin affected tablet disintegration times, simulated saliva was developed from the current art by combining electrolytes (12 mM $KH_2PO_4$, 40 mM NaCl, 1.5 mM $CaCl_2$) with porcine gastric mucin at concentrations of 20 mg/ml and 50 mg/ml and adjusting the pH to 6.2. Human saliva consists of >20 mg/ml maxillary mucin.

Coated tablets were evaluated in four solutions containing water, electrolytes and simulated saliva at 20 mg/ml and 50 mg/ml mucin. The coating started dissolving within 5-7 seconds on tablets placed in 50 ml of 23.4° C. tap water.

When tablets were placed in 50 ml of electrolyte solution (12 mM $KH_2PO_4$, 40 mM NaCl, 1.5 mM $CaCl_2$, pH 6.2, 23.5° C.), the coatings started dissolving in 5-7 seconds.

Surprisingly, tablets placed in 50 ml of high mucin simulated saliva (50 mg/ml mucin, 23.2° C.) behaved very differently. The coating for both tablets tested remained intact for 30 seconds. Delayed rupture of the coating was also demonstrated in a 20 mg/ml simulated saliva solution.

These tests were performed by immersing tablets in 50 ml of simulated saliva and represents an extreme test condition for the sake of stressing the tablets to demonstrate the differences in the way the tablets react in different solutions. These tests demonstrate the delayed rupturing activity is due to mucin present in saliva and not the electrolytes. In actual oral ingestion far less saliva is present in the oral cavity and a longer delay would be anticipated.

In nature, mucin is used by organisms to create a protective barrier for moisture retention and lubrication. The compositions of the present invention take advantage of the presence of maxillary mucin in saliva to prolong the coating protection and enable the tablet to be swallowed in a timely fashion while ensuring immediate disintegration in water.

Example 3: Disintegration

Tablets formulated with a crosslinked polyvinyl-pyrrolidone (povidone) resulted in tablets which would swell slowly, if at all, at low temperatures, and fracture into large portions that would not disintegrate further into small particles. Chilling a tablet prior to addition to cold water would slow or eliminate the disintegration of the tablet.

We further evaluated sugar disintegrants: sucrose, dextrose, mannitol. These disintegrants did not perform well in cold water. Tablets did not swell or disintegrate. However, upon examination of wetted tablets, we found that these excipients provided an improvement in the wicking of water to the interior of the tablet.

Combinations of mannitol and povidone resulted in tablets exhibiting a desired dissolution profile. By combining the wicking characteristics of mannitol with the disintegration properties of povidone, we were able to produce a tablet that would completely disintegrate in cold water. The wicking action of the mannitol draws water into the interior making it available to the povidone, thereby allowing the povidone to swell at a faster rate than the tablet can cool. The ratio of these two components was important to avoid a slowed reaction and incomplete disintegration of the tablet.

Example 4: Manufacturing Tablets

An oral pharmaceutical tablet composition was prepared according to the following steps.

1. Sodium Sulfate Sieving:

Commercial grade sodium sulfate crystals were milled on a fitzmill hammer mill with a 0.0027" screen at 1000 rpms. The milled crystals were screened on a Gyra-vibe sieve to obtain a 150-700 µm particle size cut. Any material which did not pass through the 700 µm screen was discarded. Any material which passed through the 150 µm screen was discarded. Material which remained on the 150 µm screen was retained for use.

2. Blending:

The compounds were blended in a 5 cubic foot slant cone blender. The sodium sulfate, potassium sulfate, and PEG-3350 was charged then blended for 10 minutes. The disintegrants were charged then blended into the sulfate/PEG-3350 composition for 5 minutes. Lastly, the lubricant was charged then blended into the composition for 2 minutes.

3. Compression:

The composition was compressed into tablets using a Stokes Press model 454. The press was operated at 600 TPM with a feeder speed of 70 RPM and an average final compression force of 3600 lbs. The tablets produced had an average tablet weight of 1.705 g, a thickness range of 7.10-7.21 mm and a hardness range of 7-15 kp.

4. Coating Solution:

The tablets were coated with a polyvinyl alcohol-polyethylene glycol copolymer solution (Kollicoat IR solution of 20%-25% solids). The solution was prepared by charging the polyvinyl alcohol-polyethylene glycol copolymer, adding it to water, and mixing until dissolved. Once the polymer was dissolved, a 1% solution of blue dye #1 was added for a final concentration of 0.1%.

5. Coating:

The tablets were coated on a Compulab Coater with a 24 inch rotary drum spray dryer. The coating solution was applied using a pump setting of 8-10 and a drum speed of 3.6 RPM. The atomizing air pressure was 43 psi and 475-485 CFM at 27.0° C. The tablets were coated to a 2%-6% weight gain and allowed to dry for 10 minutes in the coater.

Example 5: Exemplary Tablet Formulation

Using a process similar to that described in Example 4, but without the coating step, tablets were made using the active and inactive agents set forth in Table 1. The average weight of the tablets was 1.693 g (range, 1.65-1.72 g). The average thickness of the tablets was 7.11 mm (range, 7.06-7.16 mm). The average hardness of the tablets was 13.9 kp (range, 12.2-16.1 kp).

TABLE 1

| Tablet Formulation # 1 (particle size 150-700 µm) | |
|---|---|
| Compound | Weight (grams) |
| Sodium sulfate, particle size 150-700 µm | 11918.80 |
| Potassium sulfate | 4857.20 |
| PEG-3350 (high pressure) | 990.00 |
| Aerosil 200 | 44.00 |
| Kollidon Cl | 1237.50 |
| Kollidon CL-SF | 562.50 |

TABLE 1-continued

| Tablet Formulation # 1 (particle size 150-700 µm) | |
|---|---|
| Compound | Weight (grams) |
| Ludiflash | 2280.10 |
| Sodium stearyl fumarate | 110.00 |

Example 6: Evaluation of Tablet Disintegration Profile Using 150-700 µm Particle Size Sodium Sulfate Using a process similar to that described in Example 4, tablets were made using the active and inactive agents set forth in Table 2. The tablets were coated with Kollicoat IR at a 2.033% weight gain. The average weight of the tablets was 1.709 g (range, 1.69-1.73 g). The average thickness of the tablets was 7.13 mm (range, 7.08-7.18 mm). The average hardness of the tablets was 13.6 kp (range, 12.1-15.1 kp).

TABLE 2

| Tablet Formulation #2 (particle size 150-700 µm) | |
|---|---|
| Compound | Weight (grams) |
| Sodium sulfate, particle size 150-700 µm | 9751.80 |
| Potassium sulfate | 3974.00 |
| PEG-3350 (high pressure) | 810.00 |
| Aerosil 200 | 36.00 |
| Kollidon Cl | 1021.50 |
| Kollidon CL-SF | 460.30 |
| Ludiflash | 1865.50 |
| Sodium stearyl fumarate | 90.00 |

We evaluated the time to complete disintegration of tablets formulated using sodium sulfate with a particle size of 150-700 µm in tap water with a temperature of 15.5° C. A standard disintegration apparatus was used in accordance with USP Method <701>. The disintegration apparatus was set to 30 cycles per minute with a 6 chamber basket with wire mesh at 10 openings per inch. The endpoint for tablet disintegration was the point at which all of the tablet material passed out of the basket chamber (i.e., no material remained on the mesh). In each experiment, tablet weight, tablet thickness, time to dissolution and water temperature were measured (Table 3).

TABLE 3

| Tablet Time to Disintegration | |
|---|---|
| Tablet number | Time (mm:ss) |
| 1 | 00:51 |
| 2 | 00:59 |
| 3 | 00:45 |
| 4 | 00:59 |
| 5 | 00:52 |
| 6 | 00:32 |

Example 7: Evaluation of Disintegration Profile of Tablets Based on Particle Size We evaluated the time to complete disintegration of tablet formulations in tap water with a temperature of less than 20° C. Disintegration was performed according to the process described in Example 6. In each experiment, tablet weight, tablet thickness, time to dissolution and water temperature were measured.

The time to dissolution was measured for six tablets of tablet formulation #3 (Table 4). Tablet formulation #3 comprised 65% sulfate salts with a sodium sulfate particle size greater than 300 μm. Rapid disintegration was achieved using 15.3° C. tap water (Table 5).

TABLE 4

Tablet Formulation #3 (particle size >300 μm)

| Compound | Weight (grams) |
| --- | --- |
| Sodium sulfate, particle size >300 μm | 1391.8 |
| Potassium sulfate | 567.2 |
| PEG-3350 (high pressure) | 180.0 |
| Aerosil 200 | 6.0 |
| Kollidon Cl | 300.0 |
| Ludiflash | 360.0 |
| Kollicoat IR | 180 |
| Magnesium stearate | 15.0 |

TABLE 5

Tablet Weight and Thickness and Time to Disintegration

| Tablet number | Weight (grams) | Time (mm:ss) |
| --- | --- | --- |
| 1 | 2.07 | 00:35 |
| 2 | 2.03 | 00:27 |
| 3 | 2.06 | 00:31 |
| 4 | 2.02 | 00:22 |
| 5 | 2.04 | 00:35 |
| 6 | 2.04 | 00:35 |

The time to dissolve was measured for six control tablets (Table 6), where there was no restriction on particle size. The six control tablets were also comprised of 65% sulfate salts. The sodium sulfate, anhydrous was a fine powder and obtained from a commercial source. No sieving was performed to separate particles by size prior to formulation. The average time to dissolve in 15.6° C. tap water of these tablets was significantly higher (Table 7) as compared to those tablets formulated with sodium sulfate particles greater than 300 μm (Table 5).

TABLE 6

Control Tablet Composition (no particle size restrictions)

| Compound | Weight (grams) |
| --- | --- |
| Sodium sulfate, anhydrous | 1391.8 |
| Potassium sulfate | 567.2 |
| PEG-3350 (high pressure) | 180.0 |
| Aerosil 200 | 6.0 |
| Kollidon Cl | 300.0 |
| Ludiflash | 360.0 |
| Kollicoat IR | 180 |
| Magnesium stearate | 15.0 |

TABLE 7

Tablet Weight and Thickness and Time to Disintegration

| Tablet number | Weight (grams) | Time (mm:ss) |
| --- | --- | --- |
| 1 | 1.91 | 14:46 |
| 2 | 1.96 | 08:02 |
| 3 | 1.93 | 13:24 |
| 4 | 1.94 | 16:02 |
| 5 | 1.96 | 12;58 |
| 6 | 1.95 | 11:48 |

Example 8: Determination of Time to Complete Disintegration of Tablets at Varying Temperatures We evaluated the time to complete disintegration of tablet formulation #4 (Table 8) in tap water at temperatures ranging from 2° C. to 15° C. Disintegration was performed according to the process described in Example 6. In each experiment, tablet weight, tablet thickness, time to dissolution and water temperature were measured (Table 9). The tablets were coated with Kollicoat IR at a 1.73% weight gain.

TABLE 8

Tablet Formulation #4 (particle size 150-700 μm)

| Compound | Weight (grams) |
| --- | --- |
| Sodium sulfate, particle size 150-700 μm | 11918.84 |
| Potassium sulfate | 4857.20 |
| PEG-3350 (high pressure) | 990.00 |
| Aerosil 200 | 44.00 |
| Kollidon Cl | 1237.50 |
| Kollidon CL-SF | 562.50 |
| Ludiflash | 2280.10 |
| Sodium stearyl fumarate | 110.00 |

TABLE 9

Tablet Weight and Thickness and Time to Disintegration at Varying Temperatures

| Tablet number | Weight (grams) | Time (mm:ss) |
| --- | --- | --- |
| 2° C. | | |
| 1 | 1.77 | 01:31 |
| 2 | 1.75 | 00:45 |
| 3 | 1.71 | 01:16 |
| 4 | 1.75 | 01:23 |
| 5 | 1.70 | 01:56 |
| 6 | 1.77 | 02:00 |
| 5° C. | | |
| 1 | 1.74 | 01:07 |
| 2 | 1.76 | 01:10 |
| 3 | 1.75 | 01:30 |
| 4 | 1.74 | 01:00 |
| 5 | 1.76 | 01:22 |
| 6 | 1.75 | 01:05 |
| 8° C. | | |
| 1 | 1.77 | 00:57 |
| 2 | 1.78 | 01:00 |
| 3 | 1.75 | 00:52 |
| 4 | 1.77 | 00:48 |
| 5 | 1.76 | 00:46 |
| 6 | 1.72 | 00:55 |
| 10° C. | | |
| 1 | 1.78 | 00:49 |
| 2 | 1.74 | 00:43 |
| 3 | 1.74 | 00:39 |
| 4 | 1.75 | 00:46 |
| 5 | 1.72 | 00:38 |
| 6 | 1.78 | 00:40 |

TABLE 9-continued

Tablet Weight and Thickness and Time to Disintegration at Varying Temperatures

| Tablet number | Weight (grams) | Time (mm:ss) |
|---|---|---|
| | 15° C. | |
| 1 | 1.76 | 00:29 |
| 2 | 1.70 | 00:27 |
| 3 | 1.77 | 00:31 |
| 4 | 1.74 | 00:39 |
| 5 | 1.74 | 00:28 |
| 6 | 1.74 | 00:34 |

As set forth above, the tablets of the invention disintegrate in water at 15° C. in less than 45 seconds. The tablets of the invention further disintegrate in water at 10° C. in less than 60 seconds, for example, less than 45 seconds. The tablets of the invention further disintegrate in water at 8° C. in less than 90 seconds, for example, less than 90 seconds. The tablets of the invention further disintegrate in water at 5° C. in less than 120 seconds, for example, less than 90 seconds. The tablets of the invention further disintegrate in water at 2° C. in less than 150 seconds.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An oral pharmaceutical tablet composition comprising at least one sulfate salt,
   wherein the tablet is capable of administration by direct oral ingestion and by disintegration in water prior to oral ingestion,
   wherein the tablet comprises sodium sulfate, and
   wherein less than about 5% by weight of sodium sulfate in the tablet comprises sodium sulfate particles less than about 150 μm and greater than about 1000 μm.

2. The oral pharmaceutical tablet composition of claim 1, wherein the tablet exhibits at least one of the following features:
   (i) disintegrates in water at about 2° C. or greater in less than about 150 seconds;
   (ii) disintegrates in water at about 8° C. or greater in less than about 90 seconds;
   (iii) disintegrates in water at about 5° C. or greater in less than about 120 seconds; or
   (v) does not disintegrate in the mouth in less than about 60 seconds upon direct oral ingestion.

3. The oral pharmaceutical tablet of claim 1, wherein the tablet disintegrates in water at about 2° C. or greater in less than about 150 seconds, and wherein the tablet does not disintegrate in the mouth in less than about 30 seconds upon direct oral ingestion.

4. The oral pharmaceutical tablet of claim 1, further comprising potassium sulfate and/or magnesium sulfate.

5. The oral pharmaceutical tablet of claim 1, wherein the tablet comprises at least about 60%, 65%, 70%, 75%, 80%, 85% or 90% by weight of a sulfate salt selected from the group consisting of sodium sulfate, potassium sulfate, magnesium sulfate and combinations thereof.

6. The oral pharmaceutical tablet of claim 1, wherein the tablet has a weight of between about 1000 mg and about 2500 mg, about 1500 mg and about 2000 mg, or about 1700 mg and about 1900 mg; or has a weight of about 1800 mg.

7. The oral pharmaceutical tablet of claim 1, wherein the tablet comprises a coating, optionally comprising a copolymer of polyvinyl alcohol and polyethylene glycol.

8. The oral pharmaceutical tablet of claim 1, wherein the tablet comprises at least one excipient selected from the group consisting of a disintegrant, a binder, a glidant, a lubricant, and combinations thereof.

9. The oral pharmaceutical tablet of claim 8, wherein the tablet is characterized by at least one of the following features:
   (a) wherein the disintegrant is (i) selected from the group consisting of povidone, crosslinked polyvinylpyrrolidone, sugar, sucrose, dextrose, mannitol, and a combination thereof; (ii) a combination of mannitol and povidone; or (iii) crosslinked polyvinylpyrrolidone;
   (b) wherein the binder is selected from the group consisting of polyethylene glycol, PEG3350, PEG8000 and combinations thereof;
   (c) wherein the glidant is fumed silica; or
   (d) wherein the lubricant is selected from the group consisting of magnesium stearate, sodium stearyl fumarate, and combinations thereof.

10. The oral pharmaceutical tablet of claim 8, wherein the total excipient level is less than about 40%, 35%, 30% or 25% by weight of the tablet.

11. The oral pharmaceutical tablet of claim 1, wherein the tablet comprises at least about 70% by weight of a sulfate salt selected from the group consisting of sodium sulfate, potassium sulfate, magnesium sulfate and combinations thereof.

12. The oral pharmaceutical tablet of claim 1, wherein the tablet comprises at least about 70% by weight of sodium sulfate and potassium sulfate.

13. The oral pharmaceutical tablet of claim 1, wherein the tablet comprises at least about 40%, 45%, 50%, 55%, 57%, 60% or 65% by weight of sodium sulfate.

14. The oral pharmaceutical tablet of claim 1, wherein the tablet comprises between about 40% and about 65%, or between about 50% and about 60% by weight of sodium sulfate.

15. The oral pharmaceutical tablet of claim 1, wherein less than about 5% by weight of sodium sulfate in the tablet comprises sodium sulfate particles less than about 200 pm, 250 pm or 300 pm and sodium sulfate particles greater than about 700 pm, 750 pm, 800 pm, or 900 pm.

16. The oral pharmaceutical tablet of claim 1, wherein less than about 5% by weight of sodium sulfate in the tablet comprises sodium sulfate particles less than about 150 pm and greater than about 700 pm.

17. The oral pharmaceutical tablet of claim 1, wherein less than about 5% by weight of sodium sulfate in the tablet comprises sodium sulfate particles less than about 300 pm and greater than about 700 pm.

18. The oral pharmaceutical tablet of claim 1, wherein about 96%, 97%, 98%, or 99% by weight of sodium sulfate in the tablet comprises sodium sulfate particles that are greater than about 150 pm, 200 pm, 250 pm or 300 pm and less than about 700 pm, 750 pm, 800 pm, 900 pm or 1000 pm.

19. The oral pharmaceutical tablet of claim 1, wherein at least about 99% by weight of sodium sulfate in the tablet comprises sodium sulfate particles that are greater than about 150 pm, 200 pm, 250 pm or 300 pm and less than about 700 pm, 750 pm, 800 pm, 900 pm or 1000 pm.

20. The oral pharmaceutical tablet of claim 1, wherein at least about 99% by weight of sodium sulfate in the tablet comprises sodium sulfate particles that are greater than about 150 pm and less than about 700 pm.

21. The oral pharmaceutical tablet of claim 1, wherein at least about 99% by weight of sodium sulfate in the tablet comprises sodium sulfate particles that are greater than about 300 pm and less than about 700 pm.

22. An oral pharmaceutical tablet, comprising sodium sulfate and potassium sulfate,
wherein the tablet is capable of administration by direct oral ingestion and by disintegration in water prior to oral ingestion,
wherein the tablet disintegrates in water at about 2° C. or greater in less than about 150 seconds,
wherein the tablet does not disintegrate in the mouth in less than about 30 seconds upon direct oral ingestion,
wherein the tablet comprises a coating,
wherein less than about 5% by weight of sodium sulfate in the tablet comprises sodium sulfate particles less than about 150 μm and greater than about 1000 μm.

23. The oral pharmaceutical tablet of claim 22, wherein the tablet is characterized by at least one of the following features:
(i) wherein the tablet comprises at least about 70% by weight of sodium sulfate and potassium sulfate; and
(ii) wherein the tablet comprises a disintegrant.

24. A method of preparing the oral pharmaceutical tablet of claim 1, the method comprising the steps of
(a) blending at least one sulfate salt and at least one excipient; and
(b) compressing the resulting blend into a tablet.

25. The method of claim 24, wherein the step of blending comprises blending a batch of sodium sulfate, wherein less than about 5% by weight of the batch of sodium sulfate comprises sodium sulfate particles less than about 150 μm and greater than about 700 μm.

26. The method of claim 24, further comprising coating the tablet.

27. The method of claim 24, further comprising substantially removing sodium sulfate particles less than about 150 μm and greater than about 700 μm prior to blending.

28. The method of claim 24, wherein the excipient is selected from the group consisting of a disintegrant, a binder, a glidant, a lubricant, and combinations thereof.

29. A method for inducing laxation in a subject, the method comprising administering to the subject at least one oral pharmaceutical tablet of claim 1, thereby inducing laxation in the subject.

30. The method of claim 29, wherein the tablet is swallowed directly by the subject.

31. The method of claim 29, wherein the step of administering the tablet comprises orally ingesting an aqueous dispersion of the tablet.

32. The method of claim 29, wherein the method induces laxation without inducing a clinically significant electrolyte shift in the subject.

33. The method of claim 29, wherein the subject is administered 2, 3, 4 or 5 oral pharmaceutical tablets.

34. A method for preventing or treating constipation in a subject, the method comprising administering to the subject at least one oral pharmaceutical tablet of claim 1, thereby treating or preventing constipation in the subject.

35. The method of claim 34, wherein the method treats or prevents constipation without inducing a clinically significant electrolyte shift in the subject.

* * * * *

UNITED STATES PATENT AND TRADEMARK OFFICE
CERTIFICATE OF CORRECTION

PATENT NO. : 9,919,007 B2
APPLICATION NO. : 14/774018
DATED : March 20, 2018
INVENTOR(S) : Edmund V. Dennett, Jr. et al.

Page 1 of 1

It is certified that error appears in the above-identified patent and that said Letters Patent is hereby corrected as shown below:

In the Claims

At Column 24, in Claim 15, replace all instances of "pm" with "µm";

At Column 24, in Claim 16, replace all instances of "pm" with "µm";

At Column 24, in Claim 17, replace all instances of "pm" with "µm";

At Column 24, in Claim 18, replace all instances of "pm" with "µm";

At Column 24, in Claim 19, replace all instances of "pm" with "µm";

At Column 25, in Claim 20, replace all instances of "pm" with "µm"; and

At Column 25, in Claim 21, replace all instances of "pm" with "µm".

Signed and Sealed this
Fifteenth Day of May, 2018

Andrei Iancu
*Director of the United States Patent and Trademark Office*